United States Patent [19]

Wellems et al.

[11] Patent Number: 5,130,416
[45] Date of Patent: Jul. 14, 1992

[54] RECOMBINANT DNA CLONE CONTAINING A GENOMIC FRAGMENT OF PFHRP-II GENE FROM PLASMODIUM FALCIPARUM

[75] Inventors: Thomas E. Wellems, Rockville; Russell J. Howard, Gaithersburg, both of Md.

[73] Assignee: The United States of America as represented by the Department of Health and Human Services, Washington, D.C.

[21] Appl. No.: 518,299

[22] Filed: May 3, 1990

Related U.S. Application Data

[60] Continuation of Ser. No. 279,245, Dec. 1, 1988, abandoned, which is a division of Ser. No. 895,942, Aug. 13, 1986, abandoned.

[51] Int. Cl.⁵ ...................... C07K 13/00; C07K 15/04; A61K 39/015
[52] U.S. Cl. ..................................... 530/350; 530/395
[58] Field of Search ............... 530/350, 395, 806, 820, 530/387; 424/88; 514/12, 8

[56] References Cited

U.S. PATENT DOCUMENTS 4,707,445 11/1987 McCutchan et al. .................. 435/91
5,001,225 3/1991 Taylor ................................. 530/387

OTHER PUBLICATIONS

Wellems, T. E. and Howard, R. J. Aug. 1986, PNAS 83:6065–6069, Homologous genes encode two distinct histidine-rich proteins.
Leech, James H. et al., 1984, J. Cell. Biol. 98(4):1256–1264, See Chem. Abstract 100:172564m, *Plasmodium falciparum malaria* . . .
Merrified, B. Science, vol. 232, pp. 341–347, "Solid Phase Synthesis," 1985, See last page.
Wellems, T. E. in Molecular Strategies of Parasitic Invasion, 1987, pp. 47–58.
Brown, 1984, *Nature*, "Blood-Stage antigens Cloned".
Godson, et al., 1983, *Nature*, "Identification and Chemical Synthesis of a Tandemly Repeated Immunogenic Region of *Plasmodium knowlesi* Circumsporozoite Protein" 305:29–32.
Bellou, et al, 1985, *Science*, "Immunigencity of Synthetic Peptide from Circumsporozoite Protein of *Plasmodium faciparum*" 228:996–999.
Dame, et al., 1984, *Science*, "Structure of the Gene Encoding the Immunodominant Surface Antigen on the Sporozoite of the Human Malaria Parasite Plasmodium falciparum" 225:593–599.
Young, et al., 1985, *Science*, "Expression of *Plasmodium falciparum* Circumsporozoite Poroteins in *Escherichia coli* for Potential Use in a Human Malaria Vaccine" 228:958–962.

Primary Examiner—Margaret Moskowitz
Assistant Examiner—T. Cunningham
Attorney, Agent, or Firm—Robert Benson

[57] ABSTRACT

A histidine rich antigen, designated PfHRP-II, has been synthesized from a recombinant DNA clone containing a genomic fragment of *Plasmodium falciparum*. PfHRP-II is a protein exported from the parasite into the body fluid. This protein passes through the host erythrocyte in concentrated packets and is released from the infected erythrocyte into the body fluid. The antigen has been isolated and is useful for protection against malaria.

4 Claims, 2 Drawing Sheets

```
                                                    Intron  - Asn Asn Ser Ala
II          TAAATTTTTTCATTTTTAAATGCTTTTTTATTTTTATATAG AAT AAT TCC GCA  53

Phe Asn Asn Asn Leu Cys Ser Lys Asn Ala Lys Gly Leu Asn Leu Asn Lys Arg Leu Leu
II TTT AAT AAT AAC TTG TGT AGC AAA AAT GCA AAA GGA CTT AAT TTA AAT AAG AGA TTA TTA 113

His Glu Thr Gln Ala His Val Asp Asp Ala His His Ala His His Val Ala Asp Ala His
II CAC GAA ACT CAA GCA CAT GTA GAT GAT GCC CAT CAT GCT CAT CAT GTA GCC GAT GCC CAT 173

His Ala His His Ala His His Ala Ala Asp Ala His His Ala His His Ala Ala Asp Ala
II CAT GCT CAT CAT GCT CAC CAT GCA GCC GAT GCC CAT CAC GCT CAT CAT GCA GCC GAT GCT 233

His His Ala His His Ala Ala Asp Ala His His Ala His His Ala Ala Asp Ala His His
II CAT CAT GCT CAC CAT GCA GCC GAT GCC CAT CAC GCT CAT CAT GCA GCC GAT GCC CAT CAT 293

Ala His His Ala Ala Asp Ala His His Ala His His Ala Ala Asp Ala His His Ala His
II GCT CAC CAT GCA GCT GAT GCT CAT CAC GCT CAT CAT GCA GCC GAT GCC CAT CAT GCT CAT 353

His Ala Ala Asp Ala His His Ala His His Ala Ala Asp Ala His His Ala His His Ala
II CAT GCA GCC GAT GCC CAT CAT GCT CAC CAT GCA GCT GAT GCT CAT CAC GCT CAT CAT GCA 413

Ala Asp Ala His His Ala His His Ala Ala Tyr Ala His His Ala His His Ala Ser Asp
II GCC GAT GCC CAT CAT GCT CAT CAT GCA GCC TAT GCC CAT CAT GCT CAT CAT GCA TCC GAT 473

Ala His His Ala Ala Asp Ala His His Ala Ala Tyr Ala His His Ala His His Ala Ala
II GCT CAT CAT GCA GCT GAT GCT CAC CAT GCA GCT TAT GCC CAT CAC GCT CAT CAT GCA GCT 533

Asp Ala His His Ala Ala Asp Ala His His Ala Ala Tyr Ala His His Ala His His Ala
II GAT GCT CAT CAT GCA GCT GAT GCT CAC CAT GCA GCT TAT GCC CAT CAC GCT CAT CAT GCA 593

Ala Asp Ala His His Ala Ala Asp Ala His His Ala Thr Asp Ala His His Ala His His
II GCT GAT GCT CAT CAT GCA GCC GAT GCT CAC CAT GCA ACC GAT GCT CAT CAC GCT CAC CAT 653

Ala Ala Asp Ala His His Ala Thr Asp Ala His His Ala Ala Asp Ala His His Ala Ala
II GCA GCC GAT GCT CAC CAT GCA ACC GAT GCT CAT CAT GCA GCC GAT GCT CAC CAT GCA GCC 713

Asp Ala His His Ala Thr Asp Ala His His Ala Ala Asp Ala His His Ala Thr Asp Ala
II GAT GCT CAT CAT GCA ACC GAT GCT CAT CAT GCA GCC GAT GCT CAC CAT GCA ACC GAT GCT 773

His His Ala Ala Asp Ala His His Ala Ala Asp Ala His His Ala Thr Asp
II CAT CAT GCA GCC GAT GCT CAC CAT GCA GCC GAT GCT CAC CAT GCA ACC GAT --- --- --- 824

Ser His His       Ala His His Ala Ala Asp Ala His His Ala
II --- --- --- --- --- TCT CAT CAC --- --- GCT CAC CAT GCA GCC GAT GCT CAT CAT GCA 863

Ala Ala His His Ala Thr Asp Ala His His Ala Ala Ala His His Ala Thr Asp Ala His
II GCC GCA CAC CAT GCA ACT GAT GCT CAC CAT GCA GCC GCA CAT CAT GCA ACC GAT GCT CAC 923

His Ala Ala Ala His His                     Glu Ala Ala Thr His Cys Leu Arg His
II CAT GCA GCC GCA CAC CAC --- --- --- --- --- GAA GCC GCC ACA CAT TGC CTA CGC CAT 968

End
II TAAATTTATTTAATAATAGATTAAAAATATTATAAAAATAAAAACATAAACACAGAAATTACAAAAAAAATACATATGA 1047

II ATTTTTTTTTTGTAATCTTCCTTATAAATATAGAATAATGAATCATATAAAACATATCATTATTCATTTATTTACATTT 1126

II AAAATTATTGTTTCAGTATCTTTA                                                       1150
```

B

```
                                          Met Val Ser Phe Ser Lys Asn
         UAAAAUUAUUUAAUAAAA AUG GUU UCC UUC UCA AAA AAU

Lys Val Leu Ser Ala Ala Val Phe Ala Ser Val Leu Leu Leu Asp Asn Asn Asn Ser Ala
   AAA GUA UUA UCC GCU GCC GUU UUU GCC UCC GUA CUU UUG UUA GAU AAC AAU AAU UCC GCA

Phe Asn Asn Asn Leu Cys Ser Lys Asn Ala Lys Gly
   UUU AAU AAU AAC UUG UGU AGC AAA AAU GCA AAA GGA
```

RECOMBINANT DNA CLONE CONTAINING A GENOMIC FRAGMENT OF PFHRP-II GENE FROM PLASMODIUM FALCIPARUM

This is a continuation of application Ser. No. 07/279,245, filed Dec. 1, 1988 which in turn is a divisional Ser. No. 895,942 filed Aug. 13, 1986, both abandoned.

BACKGROUND OF THE INVENTION

1. Technical Field

The present invention is related to malarial antigens and the genes encoding the same. More particularly, the present invention is related to a recombinant DNA clone (pDL4.1) containing a genomic fragment of PfHRP-II gene from *Plasmodium falciparum*.

2. State of the Art

Of various parasitic diseases, malaria remains one of the most menacing conditions. Substantial progress has been made in identifying the pathogenic factors causing malaria and *Plasmodium falciparum* has been recognized as the major pathogen of human malarial disease.

Recent advances in biochemical, immunological and genetic technologies have led to the recognition of certain antigens and to the characterization of certain genes or gene-fragments encoding the synthesis of malarial pathogenic antigens. The present invention relates to one such discovery.

SUMMARY OF INVENTION

An object of the present invention is to provide a new, soluble, histidine-rich protein, designated PfHRPII, from *P. falciparum* infected erythrocytes.

A further object of the present invention is to provide a recombinant DNA clone containing a genomic fragment capable of encoding PfHRP-II protein.

A still further object of the present invention is to provide a method of early detection or diagnosis of malarial infection employing the PfHRP-II antigen or an antibody having specificity against said PfHRP-II antigen.

It is another object of the present invention to provide a pharmaceutical composition comprising immunogenic amount of PfHRP-II to induce protective immunity in a host to which said pharmaceutical composition is administered in a pharmaceutically acceptable vehicle or carrier.

Other objects and advantages will become evident as the detailed description of the invention proceeds.

BRIEF DESCRIPTION OF DRAWINGS

These and other objects, features and many of the attendant advantages of the invention will be better understood upon a reading of the following detailed description when considered in connection with the accompanying drawings wherein:

FIG. 2 (A) shows the genomic and deduced amino acid sequences of PfHRP-II displayed by automated plotting. The register of the open reading frame of PfHRP-II is in phase with the gene for β-galactosidase in λMAB1 as expected, since this clone produces a fusion protein reacting with both McAb87 and anti-β-galactosidase. The sequence shown for PfHRP-II does not include the nucleotides added by ligation of Eco RI linkers (GGAATTCC) to the genomic fragment during library construction.

FIG. 2(B) shows the sequence of PfHRP-II mRNA obtained by primer extension analysis. The splice junction is indicated by the arrow. The hydrophobic leader sequence is underlined;

DETAILED DESCRIPTION OF INVENTION

Figure 1:
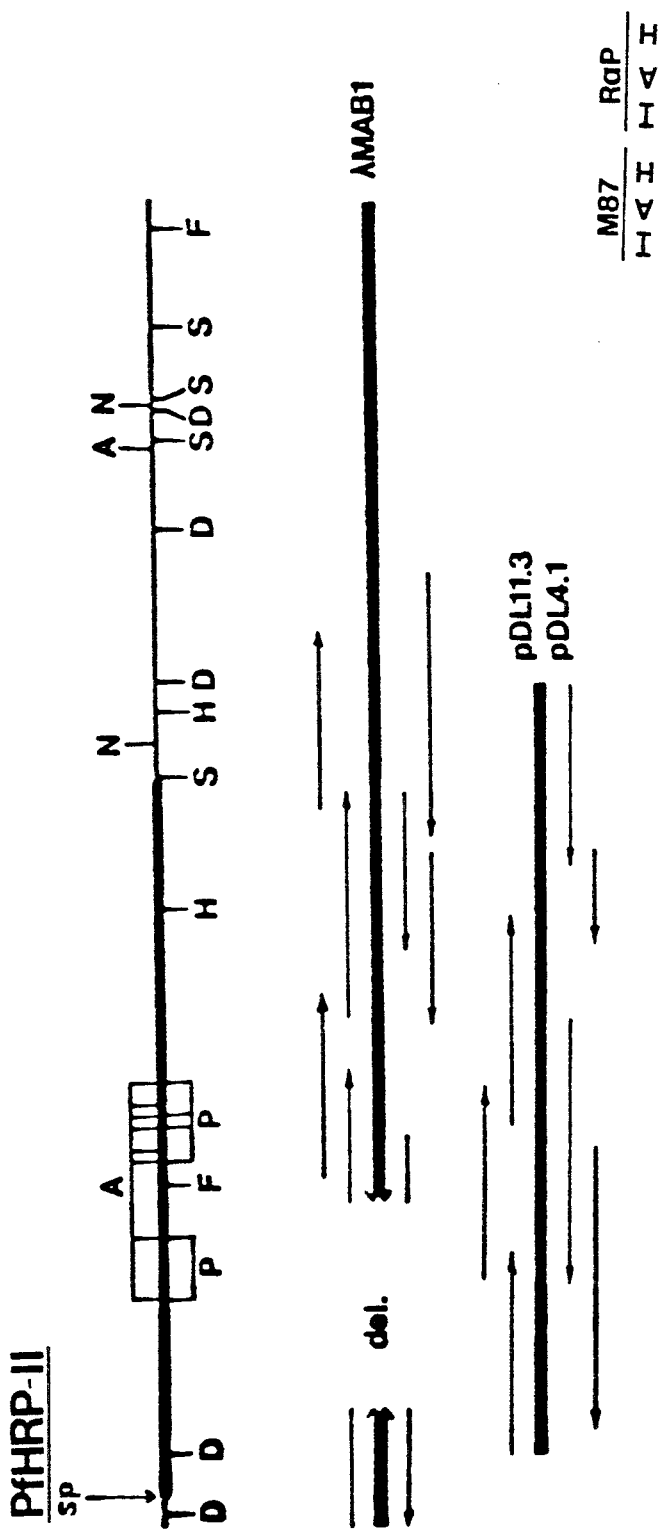
FIG. 1 shows the genomic map and sequencing strategy for PfHRP-II. Coding regions are directed from left to right and are marked by heavy lines on the genomic maps. Comparison of the Alu I and Dra I restriction fragments from genomic DNA with those from λMAB1 revealed a 279bp deletion occurring within the region of tandem repeats but the reading frame having been preserved. Restriction patterns of inserts from clones pDL4.1 and pDL11.3 were compared with corresponding restriction digests of genomic DNA by Southern blotting and showed no evidence of deletion or rearrangement. Nucleotide sequence analysis was performed on subclones in M13mp18 having targeted deletions generated by timed exonuclease III digestions. The coding strand of the pDS11.1 insert was determined from fragments digested with Pvu II and subcloned into M13mp19. Sp, splice site at 3' end of intron. A, Alu I; D, Dra I; F, Fok I; H, Hinf I; N, Nde I; P, Pvu II; S, Ssp I.

The above and various other objects and advantages of the present invention are achieved by a recombinant DNA clone (pDL4.1) containing a genomic fragment of the PfHRP-II gene from *P. falciparum*.

Unless defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

The term "PfHRP-II" as used herein means a protein whose amino acid sequence and encoding genetic map (nucleotide sequence) are shown in FIG. 2A.

A. Methods of Isolation and Characterization of the Clone

1. A genomic expression library in the vector λgt11 was constructed from *Plasmodium falciparum* DNA digested with mung bean nuclease. The description of this library and the methods of construction was the same as described by McCutchan et al. (Science 225:625–628). DNA from the 7G8 clone of the Brazil isolate IMT22 of *P. falciparum* (Burkot et al., Trans. R. Soc. Trop. Med. Hyg., 78:339–341) was used to construct the library.

2. A monoclonal antibody, McAb87, was prepared which reacts specifically with the histidine-rich protein PfHRP-II. The methods of preparation and characterization of McAb87 was the same as described by Howard et al. (J. Cell. Biol., 1986).

3. A recombinant DNA clone (λMAB1) was isolated from the genomic expression library by immunoscreening with McAb87. The methods used in the immunoscreening was the same as described by Young and Davis (Proc. Natl. Acad. Sci. USA, 80:1194-1198; Science, 222:778-782) and Dame et al. (Science 225:593-599). Immunoblot analysis of the recombinant clone showed that λMAB1 produced an inducible fusion protein of approximate Mr 144,000 which reacted with both McAb87 and anti-$\beta$-galactosidase.

4. The insert was excised with Eco RI from -λMAB1 DNA purified by gel electrophoresis and cloned into the sequencing vector M13mp18 using standard procedures (Maniatis et al., Molecular cloning: A Laboratory Manual, Cold Spring Harbor Laboratory, 1982; Yanish-Perron et al., Gene 33:103-119). Sequence analysis was performed on subclones in M13mp18 having targeted deletions generated by exonuclease III digestion. Sequences were obtained by the dideoxynucleotide method (Sanger et al., Proc. Natl. Acad. Sci. USA, 74:5463-5467) using commercially supplied reagents (Bethesda Research Laboratories, Bethesda, Md.). The sequence revealed a region of tandem repeats extending from nucleotides 148-669 predominantly encoding the oligopeptides AHH and AHHAAD, wherein A=Alanine; H =Histidine and D=Aspartic acid. Restriction analysis identified a 544 bp fragment which spanned the repeats. This fragment was purified and used to probe DNA transfer blots of genomic DNA (Southern, J. Mol. Biol. 98:503). Comparison of the restriction fragments from genomic DNA with those from λMAB1 revealed that a 279 bp deletion had occurred in the repeat region but had preserved the reading frame.

5. To obtain the complete region of tandem repeats in the PfHRP-II gene, P. falciparum DNA was restricted with the enzyme Dra I and ligated into the Sma I site of the plasmid pUC18 using standard methods (Maniatis, supra). Two clones, pDL4.1 and pDL11.3, were obtained having identical inserts oriented in opposite direction in the vector. Restriction analysis and comparative DNA transfer blotting were performed as described herein supra and showed no evidence of deletion or rearrangement.

6. RNA transfer blots were performed to confirm that the cloned DNA was transcribed. RNA was isolated from saponin purified P. falciparum parasites suspended in 100 mM NaCl, 10 mM tris pH 8.0, 2 mM MgCl$_2$, 10 mM vanadyl-ribonucleoside comlexes and 1% NaDodSO$_4$. Sequential extraction was carried out with hot phenol and chloroform according to the method of Hyde et al. (Mol. Biochem. Parasitol., 4:283-290). RNA transfer and hybridization with nick-translated pDL4.1 were performed according to the protocols described by Mehdy et al. (Cell 32:763-771).

Figure 3:
FIG. 3 shows the schematic representation of the gene for PfHRP-II. The lengths of the coding regions, represented by boxes, are drawn to scale. Intervening sequences (I) and repeat domains ($R_{II}$) are shown.

7. The complete nucleotide sequence of each insert from pDL4.1 and pDL11.3 was determined by the dideoxynucleotide method of Sanger et al, supra, and both were found to be identical. FIGS. 1, 2 and 3 show the map and sequence obtained for the region of the PfHRP-II gene extending from the 3' splice junction of the intron to and through the stop codon.

8. The nucleotide sequence of the RNA transcript extending from the initiating codon to the intron splice junction was obtained by primer extension analysis according to the protocol of Belfort et al (Cell 41:375-382). Oligonucleotide primers (synthesized as recommended by the manufacturer, Applied Biosystems DNA synthesizer, Foster City, Calif.) were used which were complementary to nucleotides 64-83 and 114-135 of the PfHRP-II genomic sequence (FIG. 2). Reactions were carried out using 0.5 pmol of 5'labelled synthetic oligonucleotide and 10 $\mu$g of P. falciparum RNA.

Figure 4:
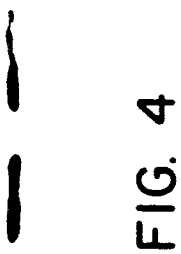
FIG. 4 shows immunoprecipitation of PfHRP-II from infected culture supernatant with McAb87(identified in FIG. 4 as M87) and rabbit antiserum (identified in FIG. 4 as RoC P) to the synthetic oligopeptide AHH-(AHHAAD)$_2$. The PfHRP-II is labelled with hu $^3$H-alanine$^{(A)}$ and $^3$H histidine$^{(H)}$ but not with $^3$H-isoleucine$^{(I)}$.

9. To confirm the reading frame and deduced amino acid sequence of PfHRP-II as correct, antisera were generated against a synthetic oligopeptide containing repeats from the deduced sequence and used to immunoprecipitate biosynthetically labelled PfHRP-II. The synthetic oligopeptide AHH(AHHAAD)$_2$ was synthesized by the solid-phase method of Merrifield and Marglin (Ann. Rev. Biochem. 39:841-866) and cleaved from the solid support with liquid HF (Tam et al., J. Am. Chem. Soc. 105:6442-6455). The oligopeptide was desalted using a Biogel P-2 column and coupled to Keyhole Limpet hemocyanin (KLH). Rabbits were immunized with biweekly injections of a 1:1 mixture of the synthetic oligopeptide, AHH(AHHAAD)$_2$, and KLH in Freund's complete adjuvant and antisera were obtained during the 7th week following the first injection. The antiserum thus obtained and McAb87 reacted with specificity with the protein (PfHRP-II) obtained from infected erythrocyte, thus demonstrating the identical nature of the synthetic and the naturally occurring PfHRP-II epitope (FIG. 4). The observed specificity of reaction between the antigen (PfHRP-II) and the antibodies indicates neutralizing efficacy of the antibodies against PfHRP-II.

10. Studies of biosynthetically labelled cultures were performed on the 7G8 clone of P. falciparum maintained in vitro by the methods of Trager and Jensen (Science, ? 93:673-675). Labelled amino acids L-[2,5-$^3$H]-histidine, L-[2,3-$^3$H]-alanine, L-[4,5-$^3$H]-isoleucine and the labelled sugar D-[6-$^3$H]-galactose were obtained from Amersham Corporation (Arlington Heights, Ill.) and used for biosynthetic labelling according to the procedures of Leech et al. (J. Cell. Biol. 98:1256-1264). Cultures were harvested after 24 hours of labelling and immunoprecipitated by standard methods (Kessler, J. Immunol. 115:1617-1624) using McAb87 and the antisera described in step 9, supra.

A deposit of the recombinant DNA clone (pDL4.1) prepared in accordance with the present invention has been made at the American Type Culture Collection, Rockville, Md. on Aug. 13, 1986 under accession number 40248. It is noted that the deposit made at the ATCC shall be viably maintained for the life of the patent if issued or for at least 30 years from the date of the deposit and made available without restriction to the public upon issuance of the patent, of course, consistent with the provisions of the law.

B. Properties of the PfHRP-II Gene and Expressed Protein

1. The PfHRP-II gene has an interrupted structure, with an intron separating a short (69 bp) exon encoding a hydrophobic leader from a 927 bp exon encoding numerous tandem repeats of very high histidine, alanine and aspartate content (FIGS. 2 and 3)

2. The gene is transcribed to produce an RNA transcript of approximately 2.1 kb.

3. The nucleotide sequence encodes a protein of approximate molecular weight 35,138, a value much lower than the Mr of 60,000-80,000 obtained by SDS-PAGE. Without being bound to any theory, possible explanations for this difference include post-translational events (e.g. dimerization) and anomalous migration during SDS-PAGE.

4. The deduced sequence contains about 34% histidine, 37% alanine and 10% aspartate.

5. PfHRP-II migrates as a multiplet of bands generally spanning 5,000-10,000 Mr which is indicative of post-translational processing.

6. The protein is exported from the parasite into the body fluid. PfHRP-II passes through the host erythrocyte in concentrated "packets" and is released from the infected erythrocyte into the body fluid in vivo or into the culture supernatant in vitro. The mature protein recovered from culture supernatant corresponds to the slowest moving band of the multiplet reactive with McAb87.

7. The mature protein is glycasylated and incorporates radiolabelled galactose.

8. The protein exhibits strong binding to the divalent cations $Zn++$ and $Cu++$ (Table 1). Binding of $Zn++$ to PfHRP-II can be reversed by imidazole, the side group of histidine. Other cations forming chelation complexes with histidine (such as Cd, Hg, Co, Ni) would likewise bind with PfHRP-II.

9. PfHRP-II binds strongly to heparin-Sepharose (Pharmacia) and cannot be eluted by a gradient of NaCl up to 2M NaCl, whereas other proteins which bind to heparin-Sepharose are eluted by $\leq 1.5$ M NaCl, indicating the polycationic nature of multiple imidazole groups of PfHRP-II.

10. Using McAb87 and/or rabbit antisera, experiments with serum from patients infected with malaria demonstrated the presence of circulating PfHRP-II in infected blood and the presence of antibodies to PfHRP-II in previously infected patients (Data not shown).

11. PfHRP-II has a histidine content that is similar to that of a Mr 30,000 fragment obtained from a histidine-rich glycoprotein (HRG) that has been isolated from normal human serum (Morgan, 1978 Biochim. Biophys. Acta. 535(2):319). HRG interacts with divalent metal ions, heparin, thrombospondin, and autorosette-forming thymocytes. Levels of HRG are decreased in immunosuppressed states indicating that HRG may be linked to immune function. The properties common to PfHRP-II and HRG indicate similarity of the functional role in vivo and that PfHRP-II may alter the physiologic role of HRG.

TABLE 1

| Protein | Binding to column | Peak width (mM imidazole) | Peak max (mM imidazole) |
|---|---|---|---|
| Elution of proteins from $Zn^{2+}$-chelated sepharose 6B by imidazole | | | |
| Bovine serum albumin | — | — | — |
| Human hemoglobin | + | 10–40 | 25 |
| Human transferrin | + | 25–100 | 75 |
| Human α2-macroglobulin | + | 75–130 | 100 |
| Human serum histidine-rich glycoprotein | + | 100–180 | 140 |
| PfHRP-II | + | 260–400 | 325 |
| Elution of PfHRP2 from $Cu^{2+}$-chelated sepharose 6B by imidazole | | | |

TABLE 1-continued

| Protein | Binding to column | Peak width (mM imidazole) | Peak max (mM imidazole) |
|---|---|---|---|
| PfHRP-II | + | ND | >450 |

In summary, the amino acid composition and the biochemical and biological properties of the PfHRP-II and its encoding gene clearly distinguish the recombinant clone from any other recombinant heretofore known.

Of course, the malarial antigen of the present invention prepared from the recombinant PfHRP-II clone or synthesized from the known amino acid sequence (FIG. 2) allows the preparation of a pharmaceutical composition comprising immunogenic amount of PfHRP-II to immunize against malaria in a host to whom said pharmaceutical composition is administered in a pharmaceutically acceptable vehicle or carrier such as physiological saline, nontoxic buffers, fillers or adjuvants and the like. Moreover, a kit comprising containers containing antigen and/or antibodies having specificity against PfHRP-II in suitable preservative medium such as physiological saline, nontoxic buffers and the like, and preferably lyophilized or cryopreserved, can be utilized by standard immunological assays, well known in the art, to detect or diagnose even low level or early malarial infection which otherwise cannot be detected by conventional methods such as thin and thick blood smears and the like. The kit may also include such standard items as microtiter plates, micropipettes, agglutination reading means and the like which are normally found in such kits. It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A histidine rich *Plasmodium falciparum* glycoprotein antigen, pfHRP-II, essentially free from other *Plasmodium falciparum* components, consisting essentially of the following amino acid sequence:

Met Val Ser Phe Ser Lys Asn Lys Val Leu Ser Ala Ala Val Phe
Ala Ser Val Leu Leu Leu Asp Asn Asn Asn Ser Ala Phe Asn Asn
Asn Leu Cys Ser Lys Asn Ala Lys Gly Leu Asn Leu Asn Lys Arg
Leu Leu His Glu Thr Gln Ala His Val Asp Asp Ala His His Ala
His His Val Ala Asp Ala His His Ala Ala His His Ala His His Ala
Ala Asp Ala His His Ala His His Ala Ala Asp Ala His His Ala
His His Ala Ala Asp Ala His His Ala His His Ala Ala Asp Ala
His His Ala His His Ala Ala Asp Ala His His Ala His His Ala
Ala Asp Ala His His Ala His His Ala Ala Asp Ala His His Ala
His His Ala Ala Asp Ala His His Ala His His Ala Ala Asp Ala
His His Ala His His Ala Ala Tyr Ala His His Ala His His Ala
Ser Asp Ala His His Ala Ala Asp Ala His His Ala Ala Tyr Ala
His His Ala His His Ala Ala Asp Ala His His Ala Ala Asp Ala
His His Ala Ala Tyr Ala His His Ala His His Ala Ala Asp Ala
His His Ala Ala Asp Ala His His Ala Thr Asp Ala His His Ala
His His Ala Ala Asp Ala His His Ala Thr Asp Ala His His Ala
Ala Asp Ala His His Ala Ala Asp Ala His His Ala Thr Asp Ala
His His Ala Ala Asp Ala His His Ala Thr Asp Ala His His Ala
Ala Asp Ala His His Ala Ala Asp Ala His His Ala Thr Asp Ser
His His Ala His His Ala Ala Asp Ala His His Ala Ala Ala His
His Ala Thr Asp Ala His His Ala Ala Ala His His Ala Thr Asp
Ala His His Ala Ala Ala His His Glu Ala Ala Thr His Cys Leu
Arg His.

2. A pharmaceutical composition comprising an immunogenic amount of the antigen of claim 1 and a pharmaceutically acceptable carrier.

3. The protein of claim 1 in unglycosylated form.

4. A pharmaceutical composition comprising an immunogenic amount of the antigen of claim 3.

* * * * *